US012708417B2

(12) United States Patent
Chan et al.

(10) Patent No.: US 12,708,417 B2
(45) Date of Patent: Aug. 18, 2026

(54) BONE SCREW

(71) Applicant: DEPUY SYNTHES PRODUCTS, INC., Raynham, MA (US)

(72) Inventors: Jason Chan, Dresher, PA (US); Ganesan Murugesan, Warsaw, IN (US); Abhishek Ekbote, Conshohocken, PA (US); Muruganandarn Mani, West Chester, PA (US); Dhilip Thiruppathi, Leeds (GB); Sivakumar Anbazhagan, Chennai (IN)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 317 days.

(21) Appl. No.: 17/823,846

(22) Filed: Aug. 31, 2022

(65) Prior Publication Data

US 2024/0065744 A1 Feb. 29, 2024

(51) Int. Cl.
*A61B 17/86* (2006.01)

(52) U.S. Cl.
CPC ........ *A61B 17/8635* (2013.01); *A61B 17/863* (2013.01)

(58) Field of Classification Search
CPC .................................................... A61B 17/863
See application file for complete search history.

(56) References Cited

U.S. PATENT DOCUMENTS

| | | | |
|---|---|---|---|
| 2,419,555 | A | 4/1947 | Fator |
| 2,847,885 | A | 8/1958 | Wagner |
| 3,044,341 | A | 7/1962 | William |
| 3,124,408 | A | 3/1964 | Oesterreicher |
| 3,130,763 | A | 4/1964 | Bernard |
| 3,738,218 | A | 6/1973 | Gutshall |
| 3,799,229 | A | 3/1974 | Johnson |
| 3,866,509 | A | 2/1975 | Kraus |
| 4,175,555 | A | 11/1979 | Herbert |
| 4,212,568 | A | 7/1980 | Minicozzi |
| 4,463,753 | A | 8/1984 | Gustilo |
| 5,019,079 | A | 5/1991 | Ross |
| 5,116,336 | A | 5/1992 | Frigg |

(Continued)

FOREIGN PATENT DOCUMENTS

| | | | |
|---|---|---|---|
| CN | 112220545 | A | 1/2021 |
| DE | 29611749 | U1 | 9/1996 |

(Continued)

OTHER PUBLICATIONS

U.S. Appl. No. 10/058,368, filed Aug. 28, 2018, Orbay et al..

(Continued)

*Primary Examiner* — David W Bates
(74) *Attorney, Agent, or Firm* — Kramer & Amado, P.C.

(57) ABSTRACT

A medical screw, including: a first region comprising a constant diameter first root having a first diameter and a constant pitch multi-start thread; a second region forming a transition region; and a third region including a constant diameter root having the first diameter and a constant pitch thread, wherein the transition region is in between the first region and the second region and joins the first region with the second region, and wherein a lead of the constant pitch multi-start thread is different from a lead of the constant pitch thread.

6 Claims, 7 Drawing Sheets

(56) References Cited

U.S. PATENT DOCUMENTS

| | | | | |
|---|---|---|---|---|
| 5,120,172 | A | 6/1992 | Wakai | |
| 5,259,398 | A * | 11/1993 | Vrespa | A61C 8/0089 411/413 |
| 5,403,136 | A * | 4/1995 | Mathys | A61C 8/0022 411/413 |
| 5,456,685 | A | 10/1995 | Huebner | |
| 5,562,672 | A | 10/1996 | Huebner et al. | |
| 5,593,410 | A | 1/1997 | Vrespa | |
| 5,665,087 | A | 9/1997 | Huebner | |
| 5,782,442 | A | 7/1998 | Kwak et al. | |
| 5,871,486 | A | 2/1999 | Huebner et al. | |
| 5,897,319 | A | 4/1999 | Wagner et al. | |
| 5,964,768 | A | 10/1999 | Huebner | |
| 6,001,101 | A | 12/1999 | Augagneur et al. | |
| 6,030,162 | A * | 2/2000 | Huebner | A61B 17/8863 411/413 |
| 6,129,730 | A * | 10/2000 | Bono | A61C 8/0025 606/291 |
| 6,261,292 | B1 | 7/2001 | Diebold et al. | |
| 6,299,615 | B1 | 10/2001 | Huebner | |
| 6,306,140 | B1 | 10/2001 | Siddiqui | |
| 6,398,786 | B1 | 6/2002 | Sesic | |
| 6,402,757 | B1 | 6/2002 | Moore, III et al. | |
| 6,468,277 | B1 | 10/2002 | Justin et al. | |
| 6,505,799 | B1 | 1/2003 | Bercaw et al. | |
| 6,854,942 | B1 | 2/2005 | Hargis | |
| 6,984,235 | B2 | 1/2006 | Huebner | |
| 7,037,309 | B2 | 5/2006 | Weil et al. | |
| 7,189,045 | B2 | 3/2007 | McGovern et al. | |
| 7,347,403 | B2 | 3/2008 | Belcourt et al. | |
| 7,582,107 | B2 | 9/2009 | Trail et al. | |
| 7,708,738 | B2 | 5/2010 | Fourcault et al. | |
| 7,731,738 | B2 | 6/2010 | Jackson et al. | |
| 8,070,786 | B2 | 12/2011 | Huebner et al. | |
| 8,128,671 | B2 | 3/2012 | Taylor | |
| 8,147,531 | B2 | 4/2012 | Corrao et al. | |
| 8,216,243 | B2 | 7/2012 | Yevmenenko et al. | |
| 8,267,977 | B2 | 9/2012 | Roth | |
| 8,273,113 | B2 | 9/2012 | Frenk et al. | |
| 8,303,634 | B2 | 11/2012 | Martin | |
| 8,394,132 | B2 | 3/2013 | Lewis et al. | |
| 8,460,349 | B2 | 6/2013 | Frenk et al. | |
| 8,511,958 | B2 | 8/2013 | Chang | |
| 8,540,726 | B2 | 9/2013 | Yevmenenko et al. | |
| 8,647,038 | B2 | 2/2014 | Gong et al. | |
| 8,668,726 | B2 | 3/2014 | Martin | |
| 8,945,193 | B2 | 2/2015 | Kirschman | |
| 8,979,911 | B2 | 3/2015 | Martineau et al. | |
| 8,992,587 | B2 | 3/2015 | Kirschman | |
| 9,011,505 | B2 | 4/2015 | Prandi et al. | |
| 9,078,716 | B2 | 7/2015 | Pech | |
| 9,113,976 | B2 | 8/2015 | Yevmenenko et al. | |
| 9,161,793 | B2 | 10/2015 | Huebner | |
| 9,265,540 | B2 | 2/2016 | Kirschman | |
| 9,504,504 | B2 | 11/2016 | Prandi et al. | |
| 9,554,916 | B2 | 1/2017 | Miller | |
| 9,861,413 | B2 | 1/2018 | Palmer et al. | |
| 9,901,379 | B2 | 2/2018 | Reed | |
| 10,058,368 | B2 * | 8/2018 | Orbay | A61B 17/863 |
| 10,130,406 | B2 * | 11/2018 | Castaneda | A61B 17/863 |
| 10,130,407 | B2 * | 11/2018 | Castaneda | A61B 17/8888 |
| 2002/0127085 | A1 | 9/2002 | Field | |
| 2004/0068261 | A1 | 4/2004 | Fourcault et al. | |
| 2005/0107791 | A1 | 5/2005 | Manderson | |
| 2006/0173462 | A1 * | 8/2006 | Kay | A61B 17/863 606/907 |
| 2007/0025827 | A1 | 2/2007 | Pryor | |
| 2007/0233122 | A1 * | 10/2007 | Denis | A61B 17/7032 606/247 |
| 2007/0269288 | A1 | 11/2007 | Palm | |
| 2008/0132958 | A1 | 6/2008 | Pech et al. | |
| 2008/0249579 | A1 * | 10/2008 | Taylor | A61B 17/863 606/301 |
| 2008/0292429 | A1 * | 11/2008 | Hasenbohler | A61B 17/863 411/413 |
| 2008/0300639 | A1 * | 12/2008 | Martin | A61B 17/8645 606/301 |
| 2009/0048633 | A1 | 2/2009 | Eom | |
| 2009/0118773 | A1 | 5/2009 | James | |
| 2009/0143824 | A1 * | 6/2009 | Austin | A61B 17/74 606/301 |
| 2010/0069970 | A1 | 3/2010 | Lewis et al. | |
| 2010/0174323 | A1 | 7/2010 | Fourcault et al. | |
| 2011/0070558 | A1 * | 3/2011 | Park | A61C 8/0025 433/174 |
| 2011/0106157 | A1 * | 5/2011 | Melkent | A61B 17/863 606/246 |
| 2011/0144703 | A1 * | 6/2011 | Krause | A61B 17/869 606/309 |
| 2011/0318137 | A1 | 12/2011 | Chen | |
| 2012/0022603 | A1 | 1/2012 | Kirschman | |
| 2012/0083847 | A1 * | 4/2012 | Huebner | A61B 17/863 606/291 |
| 2012/0130433 | A1 | 5/2012 | Huebner | |
| 2012/0197311 | A1 | 8/2012 | Kirschman | |
| 2014/0012334 | A1 * | 1/2014 | Armstrong | A61B 17/863 606/312 |
| 2014/0012335 | A1 | 1/2014 | Christen et al. | |
| 2014/0277188 | A1 | 9/2014 | Poulos | |
| 2014/0277190 | A1 | 9/2014 | Splieth et al. | |
| 2015/0150613 | A1 * | 6/2015 | Gauneau | A61B 17/8625 606/315 |
| 2015/0201984 | A1 * | 7/2015 | Orbay | A61B 17/8625 606/304 |
| 2015/0359573 | A1 | 12/2015 | Adams et al. | |
| 2016/0015438 | A1 | 1/2016 | Elleby et al. | |
| 2016/0030097 | A1 * | 2/2016 | Mildner | A61B 17/863 606/304 |
| 2016/0038203 | A1 * | 2/2016 | Huebner | A61B 17/844 606/304 |
| 2016/0166300 | A1 * | 6/2016 | Peukert | A61B 17/863 606/317 |
| 2016/0213412 | A1 | 7/2016 | Palmer et al. | |
| 2016/0287301 | A1 | 10/2016 | Mehl et al. | |
| 2017/0095279 | A1 * | 4/2017 | Bare | A61B 17/8057 |
| 2017/0100163 | A1 | 4/2017 | Palmer et al. | |
| 2017/0100171 | A1 | 4/2017 | Palmer et al. | |
| 2017/0151061 | A1 | 6/2017 | Lavi | |
| 2017/0196608 | A1 * | 7/2017 | Castaneda | A61B 17/84 |
| 2017/0196612 | A1 * | 7/2017 | Castaneda | A61B 17/864 |
| 2017/0296245 | A1 | 10/2017 | Gault et al. | |
| 2017/0348033 | A1 * | 12/2017 | Varner | A61B 17/8605 |
| 2018/0028245 | A1 * | 2/2018 | Ziemek | A61B 17/8695 |
| 2018/0092677 | A1 * | 4/2018 | Peterson | A61B 17/844 |
| 2018/0206897 | A1 | 7/2018 | Palmer | |
| 2019/0008570 | A1 | 1/2019 | Rowe et al. | |
| 2019/0262047 | A1 * | 8/2019 | Sommers | A61B 17/8875 |
| 2019/0357950 | A1 | 11/2019 | Bernstein | |
| 2020/0093525 | A1 * | 3/2020 | Zastrozna | A61B 17/866 |
| 2020/0405329 | A1 * | 12/2020 | Liu | A61B 17/8886 |
| 2021/0022873 | A1 * | 1/2021 | Patel | C22C 14/00 |
| 2021/0315618 | A1 * | 10/2021 | Lacaze | A61B 17/8685 |
| 2022/0079642 | A1 * | 3/2022 | Conley | A61B 17/809 |
| 2023/0190348 | A1 * | 6/2023 | Touchet | A61B 17/7291 606/317 |
| 2023/0389965 | A1 * | 12/2023 | Heuer | A61B 17/8615 |

FOREIGN PATENT DOCUMENTS

| | | | |
|---|---|---|---|
| EP | 425358 | A1 | 5/1991 |
| EP | 425358 | B1 | 1/1994 |
| EP | 1273273 | A2 | 1/2003 |
| EP | 1273273 | A3 | 6/2003 |
| EP | 1273273 | B1 | 9/2005 |
| FR | 2713291 | A1 | 6/1995 |
| FR | 2713291 | B1 | 2/1996 |
| FR | 2840799 | A1 | 12/2003 |
| FR | 2840799 | B1 | 7/2005 |
| FR | 3000663 | A3 | 7/2014 |
| FR | 3000663 | B3 | 7/2014 |

(56) References Cited

FOREIGN PATENT DOCUMENTS

| | | | |
|---|---|---|---|
| WO | WO1994020040 | A1 | 12/1899 |
| WO | WO2009130415 | A2 | 10/2009 |
| WO | WO2009130415 | A3 | 12/2009 |

OTHER PUBLICATIONS

U.S. Appl. No. 10/130,406, filed Nov. 20, 2018, Castaneda et al..
U.S. Appl. No. 10/130,407, filed Nov. 20, 2018, Castaneda et al..
U.S. Appl. No. 11/076,901, filed Aug. 3, 2021, Zastrozna.
International Search Report mailed on Jan. 9, 2024 for PCT/IB2023/058402.

* cited by examiner

BONE SCREW

TECHNICAL FIELD

Various exemplary embodiments disclosed herein relate generally to bone screws.

BACKGROUND

Bone screws may be used in connection with surgery or other procedures on a patient. These may include fixation of intra-articular Fractures, extra-articular fractures and avulsions, non-union and osteotomies of small bones and small bone fragments as well as arthrodesis of small bone joints such as the foot, hand, patella, the ulnar styloid, the capitellum, the radial head and radial styloid.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a medical screw, including: a first region comprising a constant diameter first root having a first diameter and a constant pitch multi-start thread; a second region forming a transition region; and a third region including a constant diameter root having the first diameter and a constant pitch thread, wherein the transition region is in between the first region and the second region and joins the first region with the second region, and wherein a lead of the constant pitch multi-start thread is different from a lead of the constant pitch thread.

Various embodiments are described, further including a fourth region including a constant diameter root having a second diameter greater than the first diameter and a taper region and the constant pitch thread, wherein the transition region transitions from the first diameter for the third region to the second diameter of the fourth region.

Various embodiments are described, further including a driving feature on the fourth region.

Various embodiments are described, wherein the constant pitch multi-start thread is a double-start thread.

Various embodiments are described, wherein the constant pitch multi-start thread and the constant pitch thread have the same pitch.

Various embodiments are described, wherein the third region is single threaded.

Various embodiments are described, wherein the second region is a non-threaded region.

Various embodiments are described, wherein the second region includes a thread joining of one of the threads of the first region with the thread of the third region.

Various embodiments are described, further including a cutting tip on the first region.

Further various embodiments relate to a medical screw, including: a first region including a constant diameter root with a first diameter and a constant pitch thread; a second region including a constant diameter root with the first diameter and a variable thread pitch that joins continuously to the constant pitch thread; and a third region having a tapered root with a tapered diameter and a variable pitch thread that joins continuously to the variable pitch thread of the second region.

Various embodiments are described, further including a cutting tip on the first region.

Various embodiments are described, further including a driving feature on the third region.

Various embodiments are described, wherein the first region is a distal region and is adjacent the second region at one end thereof.

Various embodiments are described, wherein the third region is a proximal region and is adjacent the second region at the other end thereof.

Various embodiments are described, wherein the largest root diameter in the third region is greater than or equal to an outer diameter of the constant pitch thread in the first region.

Further various embodiments relate to a medical screw, including: a first region including a constant diameter root with a first diameter and a constant pitch thread; a second region including a constant diameter root with the first diameter and a first variable pitch thread; a third region including a constant diameter root with a second diameter and a second variable pitch thread; and a fourth region including a step between the second and third regions, wherein the second diameter is larger than the first diameter.

Various embodiments are described, wherein the step includes a cutting surface.

Various embodiments are described, wherein the step is threadless.

Various embodiments are described, wherein the constant pitch thread in the first region joins continuously with the first variable pitch thread in the second region.

Various embodiments are described, wherein the first region further includes a fourth region having a tapered root with a tapered diameter.

Various embodiments are described, wherein the constant pitch thread in the first region has an outer diameter less than an outer diameter of the first variable pitch thread in the second region.

Various embodiments are described, wherein an outer diameter of the constant pitch thread in the first region is less than or equal to the second diameter.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Cannulated Compression Headless screw (CCHS) implants are intended for good fixation of fusion procedures and wide range of osteotomies. CCHS with a fully threaded design are intended for fixation of intra-articular fractures, extra-articular fractures and avulsions, non-union and osteotomies of small bones and small bone fragments as well as arthrodesis of small bone joints such as the foot, hand, patella, the ulnar styloid, the capitellum, the radial head and radial styloid, etc.

While terms in this application refer to their meaning to one skilled in the art, the following general examples of meanings are provided to elaborate on their general use in this application.

Pitch refers to the distance from the crest of one thread to the next. See 122 in FIG. 1B.

Crest refers to the topmost surface joining the two sides of the thread.

Root refers to the bottom of the groove between two flanks, in threaded regions. This is also referred in interchangeably as the shaft.

Osteotomy refers to a surgical operation whereby a bone is cut to shorten or lengthen it or to change its alignment.

Avulsion refers to an injury in which a body structure is torn off by either trauma or surgery.

Arthrodesis refers to surgical immobilization of a joint by fusion of the bones.

Distal refers to the leading end of the screw.

Proximal refers to the trailing end of the screw.

In the embodiments shown, the thread heights (distance from crown to root) are constant along the screw in all regions; however differing thread heights or tapered thread heights can be provided. The crest width also is constant along the threaded regions; however variable crest widths may be used. Also, each embodiment may be cannulated or not cannulated. If cannulated, there would be some predrilling of the bone for the cannula wire. Also although the embodiments are illustrated with flat proximal ends, the various features illustrated in the embodiments may be applied to a fastener with a head on their proximal end.

Figure 1A:
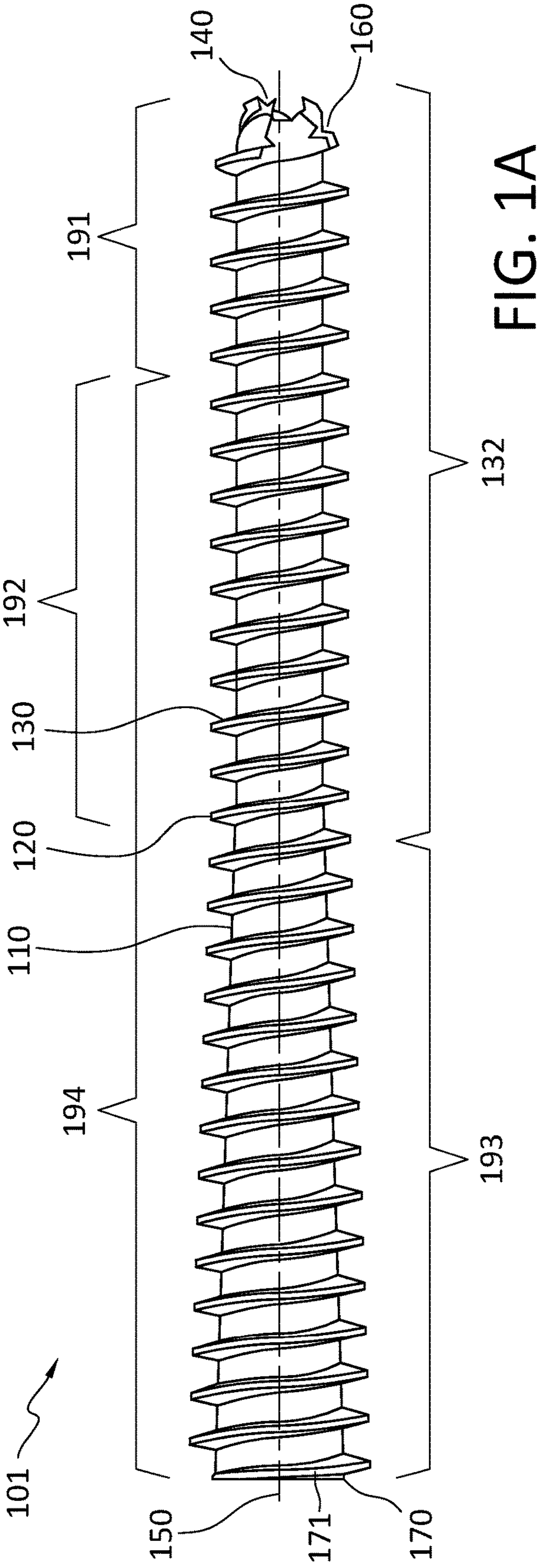
FIG. 1A is a side view of a bone screw.
Figure 1B:
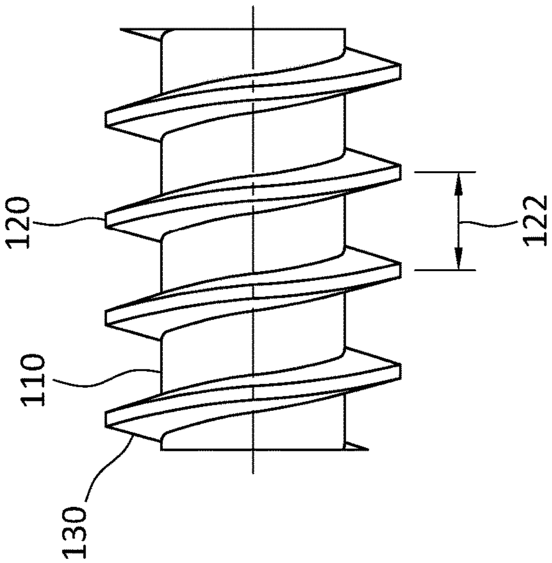
FIG. 1B is a detail view of a portion of the bone screw of FIG. 1A.
Figure 1C:
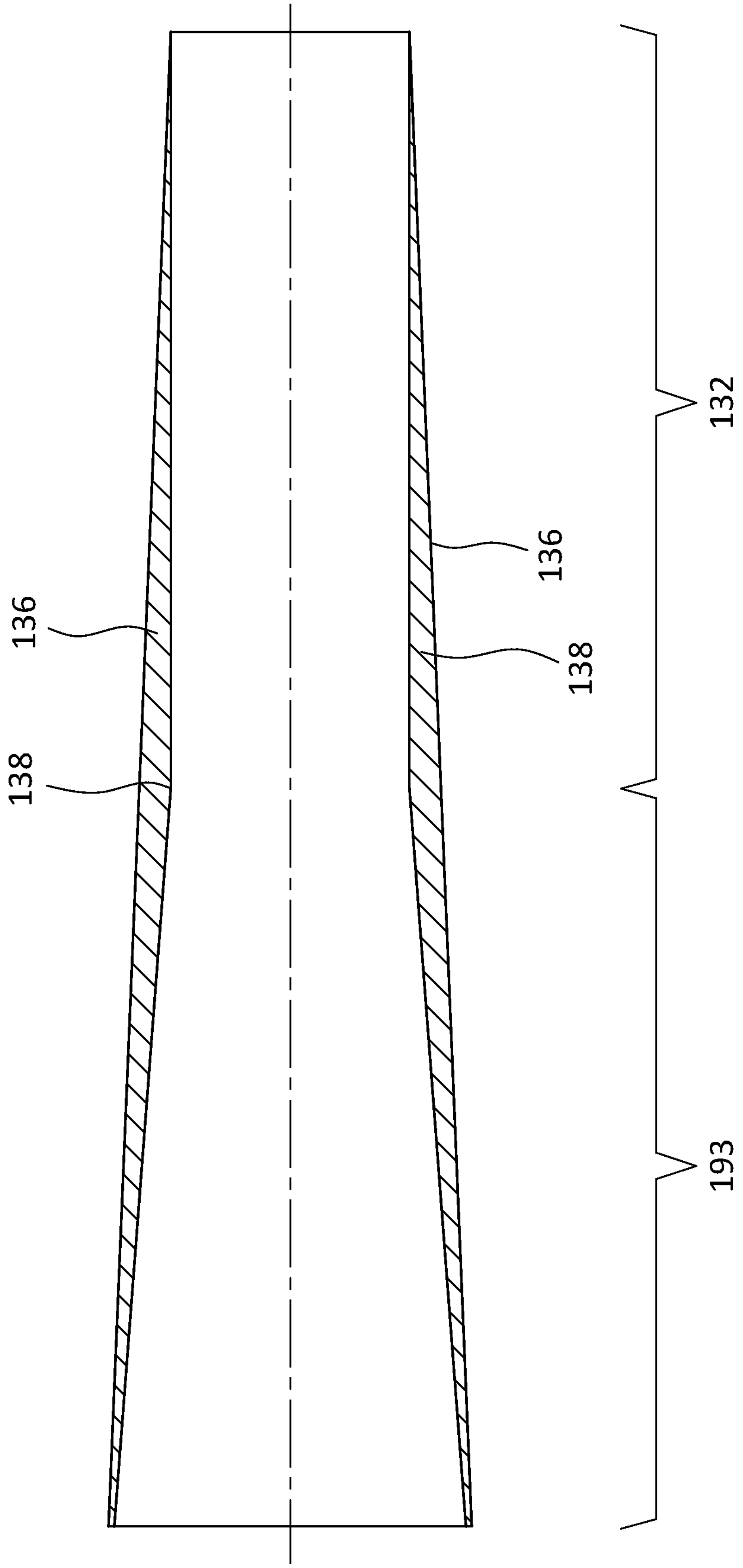
FIG. 1C is a schematic view of a shaft portion of the bone screw of FIG. 1A.

FIGS. 1A through 1C show a bone screw 101 in accordance with some embodiments. FIG. 1A is a side view of a bone screw 101. The bone screw 101 is centered on an axis 150. The bone screw has a root 110 having a continuous screw thread 130 formed thereon with constant pitch shown in region 191 and variable pitch in region 194. The root portion 110 has a distal end 160 and a proximal end 170. As can be seen in FIG. 1A, the diameter of distal end 160 is less than diameter of proximal end 170. The thread 130 extends continuously between distal end 160 and proximal end 170.

The thread 130 has a constant outer diameter for a particular length in region 132 where the root 110 diameter is constant and then the diameter of the thread 130 and the root 110 increases in region 193 until the proximal end 170 to form a substantial angle. The outer diameter is measured between an axis 150 and a crest 120 of the thread 130.

The root portion 110 has a constant root diameter in the region 132 from the distal end 160 and tapers in region 193 after certain length towards the proximal end 170. The taper is important for two reasons. First, in the tapered root region 193, i.e., the variable shaft diameter portion, each succeeding portion of the thread in region 194 is spaced further radially outwardly as a result of the taper and therefore the outer or portion of each thread in region 194 (that portion closely adjacent the crest) cuts into new bone which was not cut by the preceding thread. This provides a better purchase than would a thread having a continuously varying pitch on a cylindrical root. In this example configuration, each succeeding thread cuts additional bone within the generally cylindrical volume defined by the outside diameter of the threads.

Second, the tapered root region 193 in some embodiments provides that the radially outer surface of the root, i.e., the portion between adjacent threads, is tightly urged against uncut bone defining the wall of bore. In some embodiments, all surfaces of bone screw 101 are tightly urged against adjacent bone, rather than a space cut by a thread, in order to increase purchase of the screw.

The crest width of the thread remains constant throughout the screw, but it may vary in alternative embodiments. The pitch 122 of the thread 130, i.e., the distance from one point on the thread to the corresponding point on an adjacent thread measured parallel to axis 150 is shown in FIG. 1B. In the embodiment of FIG. 1B, the pitch remains constant from distal end 160 for approximately 5 turns as shown in region 191 and then the pitch decreases from the end of region 191 towards the proximal end 170 in region 194. The constant pitch is distributed along the constant shaft diameter of the root 110 in region 191, and the variable pitch region 194 extends across both the constant diameter region 192 and tapered root region 193 of the root 110. The thread height, i.e., the distance between crest 120 and the radially outer surface of root 110 remains constant along the length of the bone screw 101. In alternative embodiments, the thread height may vary. The bone screw 101, in this and other embodiments may include a drive socket 171 at the proximal end 170 and a self-drilling tip 140 at the distal end 160. A central bore may extend through the screw to facilitate installation of the screw over a guide wire, as in a cannulated arrangement.

In an alternative embodiment, the variable pitch region 194 may instead be a constant pitch region as well, but with a pitch less than the constant pitch of region 191.

FIG. 1B shows a detail of the root 110, thread 130, crest 120, and root 110 or shaft in a constant diameter region. The pitch 122 of the thread 130 is also shown. The constant crest width aids in minimum or no burr formation in the thread 130. Further during installation of the bone screws into the bone, a minimum crest width/land ensures that there is no deformation of the thread. Deformation of threads is common if the threads are sharp. The constant thread height throughout is beneficial for extra purchase into the bone and good retention force, but a varying thread height may be used in alternative embodiments.

Turning to FIG. 1C the taper region 193 starts when additional purchase is desired. Hence bone material is saved as compared to a fully tapered screw that is represented by lines 136 in FIG. 1C. For the same retention force, this embodiment removes less bone material when compared to the fully tapered screw which is represented by lines 136. The area 138 is the additional bone cut of a fully tapered screw when compared with the current embodiment. The outer diameter of the thread in the distal end may be larger than the diameter of the root portion in the proximal end as seen in FIG. 1C. This ensures the root portion urges with the cut bone surface made by the distal end.

The bone screw 110 has a constant shaft diameter region 132 with constant pitch thread in region 191 from the distal end 160. This may provide secure engagement with bone at the distal end 160. Further the screw tapers at region 193 and the thread pitch begins to vary continuously in region 194 thereby ensuring cutting into fresh bone and increased retention force. Because of the change in pitch between region 191 and region 194, separate bone portions engaged with each region respectively, will be drawn together because the screw advances through the separate bone portions at different rates. This allows for the separate bone portions to be compressed together to facilitate healing of broken bones or the fusion of the bone portions. Thus, in some embodiments, the combination of constant pitch at the distal end and variable pitch with taper at the proximal end provides good compression force with bone when compared with a fully continuously tapering variable pitch bone screw. Further the constant pitch at the distal end ensures complete bone contact with the screw as opposed to a continuously tapered bone screw that will have lesser bone contact when moving from distal end to proximal end.

The thread heights (distance from crown to root) are constant along the screw in all regions; however differing thread heights or tapered thread heights can be provided. The crest width also is constant along the threaded regions; however variable crest widths may be used.

The location of transition between constant pitch in region 191 and variable pitch in region 194 may occur anywhere along the length of the screw, and the location of the taper can occur anywhere along the length of the screw. Accordingly, any combination of change in pitch (of the threads), or change in diameter (taper of the root) may be used. The selection of the location of the taper and the change in pitch may chosen to address different variations in the application of the bone screw 101.

The embodiments of bone screw 101 may can provide improved compression force, good thread engagement with the bone due to constant thread height at the distal end, good distal thread engagement due to constant pitch, good pullout resistance, good bending strength, low thread deformation, low sharp edge/burr in the thread crest, and low bone removal.

Figure 2A:
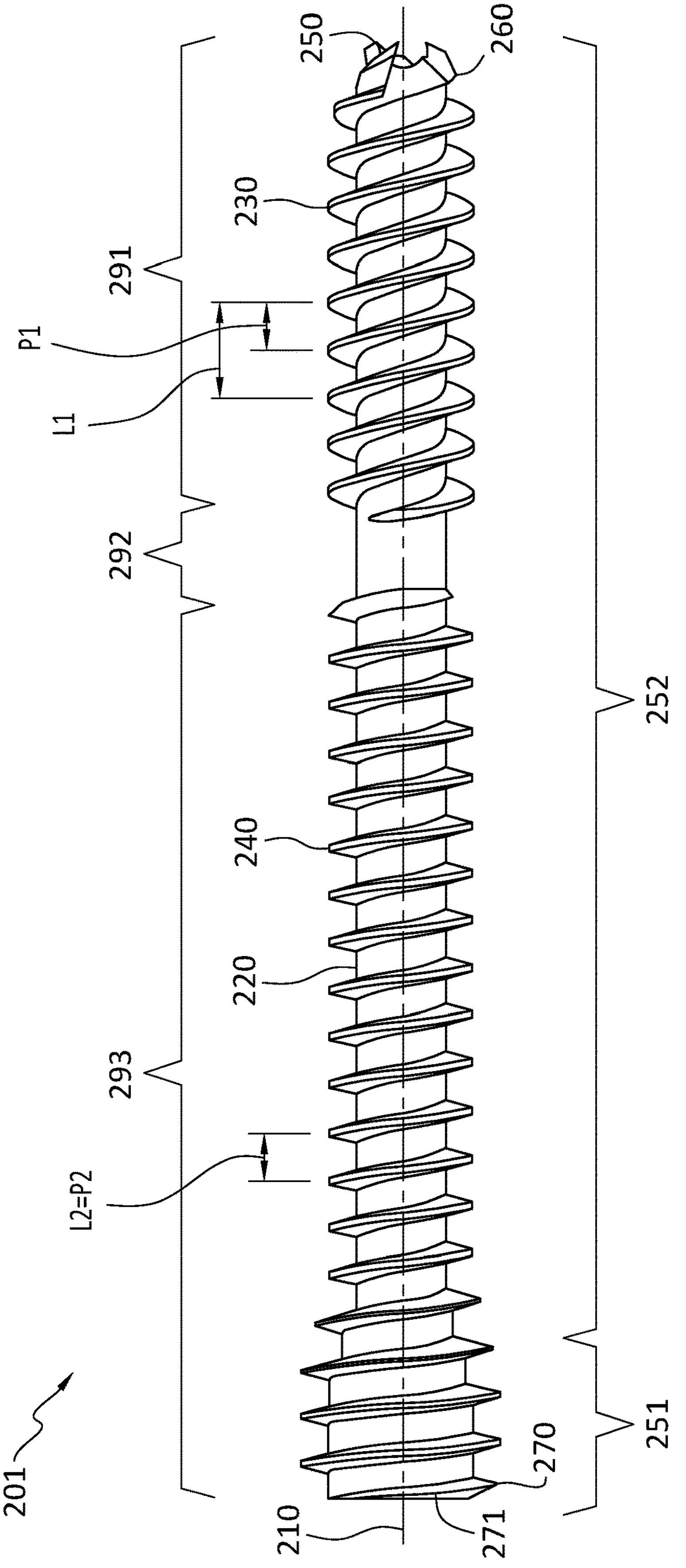
FIG. 2A is a side view of a bone screw.
Figure 2B:
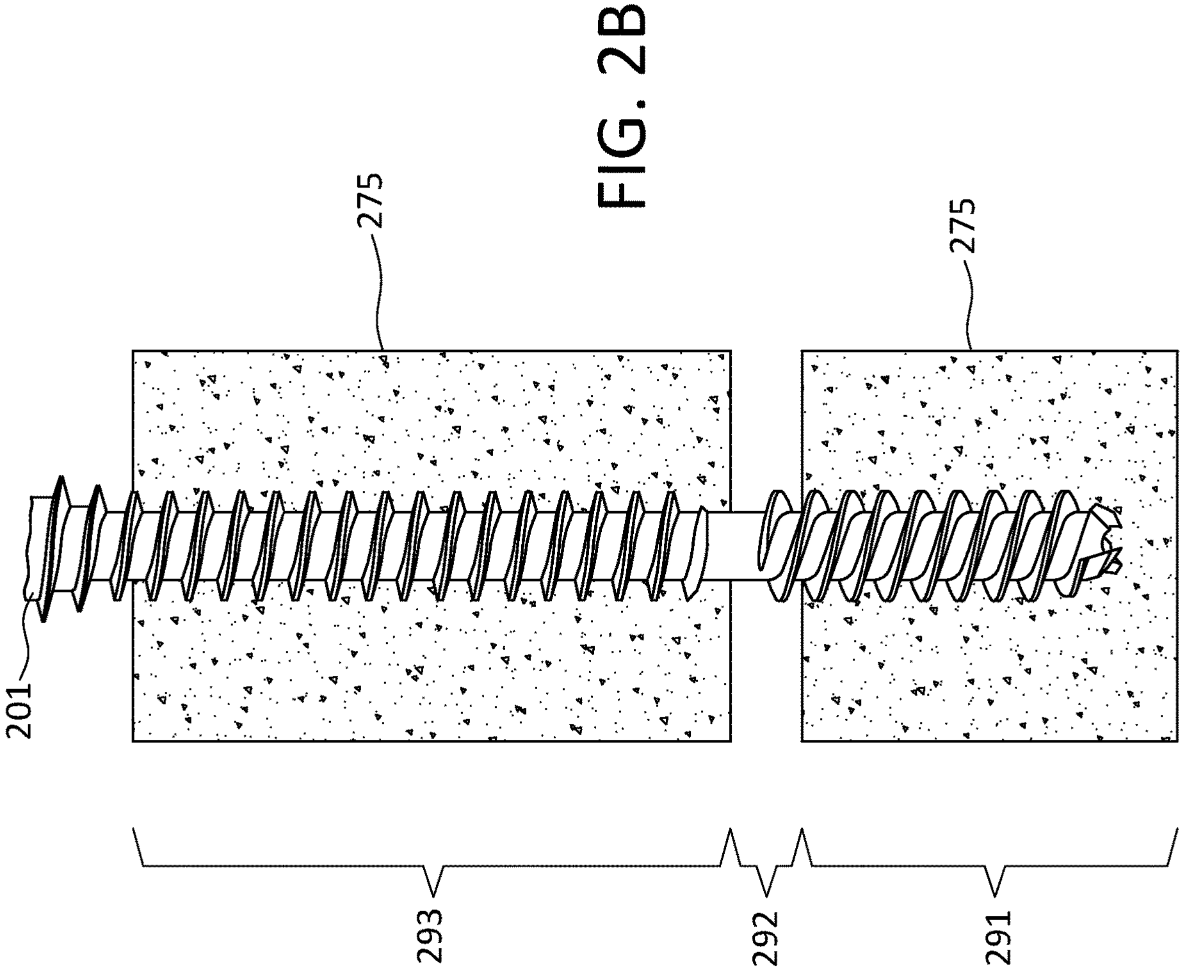
FIG. 2B is a side schematic view of the bone screw of FIG. 2A, showing the screw connecting to bone portions.
Figures 2C, 3A:
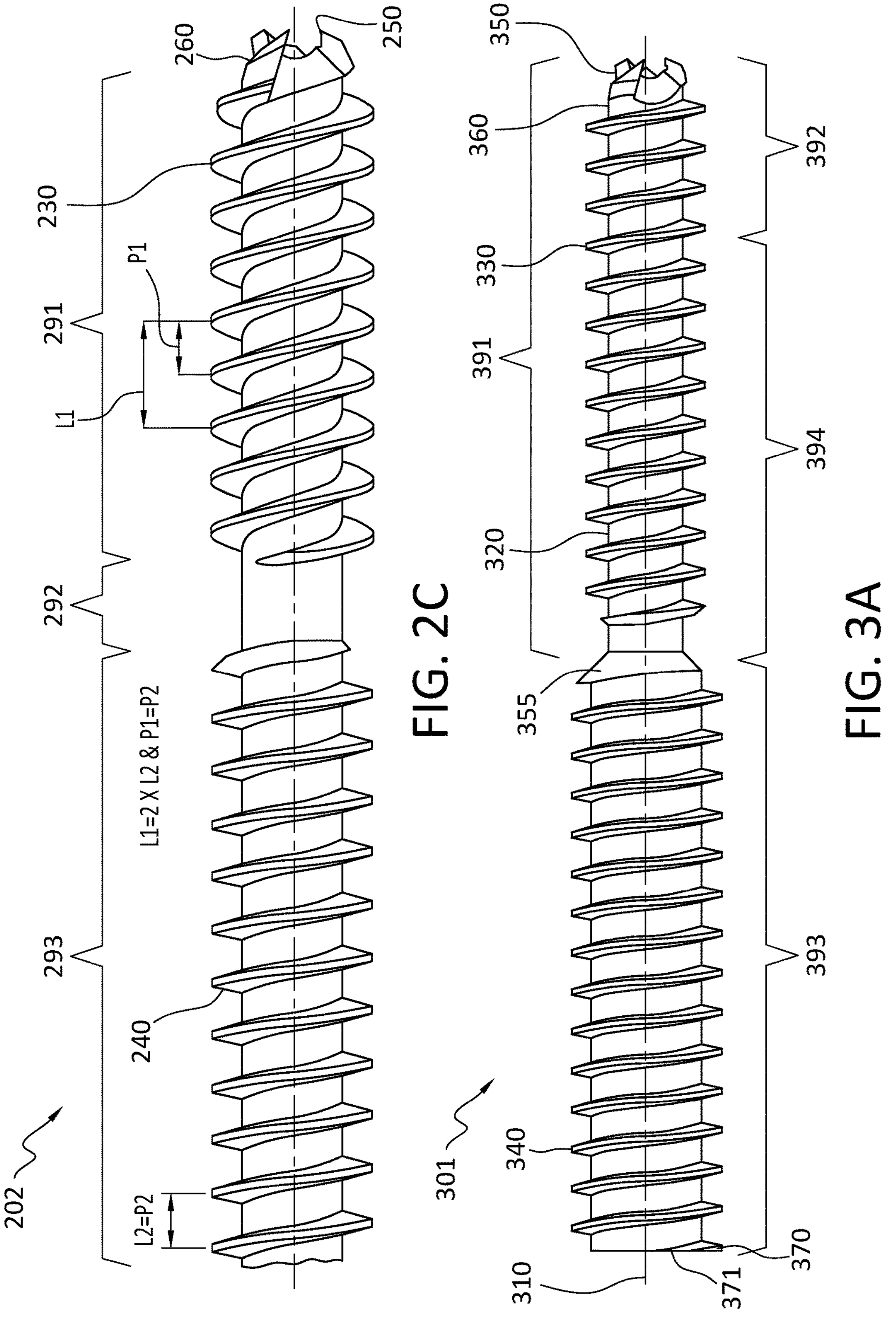
FIG. 2C shows another embodiment of a bone screw using a multi-start thread.
FIG. 3A is a side view of a bone screw.

FIGS. 2A through 2C show bone screws constructed in accordance with some additional embodiments. The bone screw 201 is centered on a longitudinal axis 210. The bone screw 201 has a root 220 that includes a distal end 260 with the self-cutting tip 250 and a proximal end 270 with a screwdriver socket 271 or driving feature. Also, the root portion 220 has a constant diameter for the majority of its length in region 252 starting from the distal end 260 and then has a tapered region 251 near the proximal end 270 which may accommodate the screwdriver socket 271. The tapered region 251 may also help to facilitate the increase of purchase between the bone and the bone screw 201 as described above.

The bone screw 201 includes a constant pitch, double-start, constant root diameter and constant outer diameter region 291, the transition zone 292 that is an unthreaded constant diameter region, and a constant pitch, single-start, partially or fully variable diameter region 293 having a constant or variable root diameter and a constant thread height above the root; thus the outer edges of the threads may have a constant or variable diameter. The transition zone 292 is adjacent to the region 291 and region 293. The transition zone 292 which is not threaded can have a tapered diameter instead of a constant diameter. Each or both of region 291 and region 293 may be partially or fully tapered, and one or both can have a constant root and/or thread diameter.

The double-start thread 230 in region 291 is provided where two threads having the same dimension start 180° ahead of the other. The threads 230 terminate in a transition zone 292 where threads are not present to avoid sudden pitch change in one of the double-start thread and to smoothen the stopping point of another start thread. In an alternative embodiment, one of the double started threads 230 may continue through the transition zone 293 and become the thread 240. The transition zone 292 may be a regular cylinder or may have one or more tapers. The double-start thread 230 may also be a multi-start thread including three or more intertwined threads running parallel to one another. Intertwining threads allow the lead distance of a thread to be increased without changing its pitch. A double-start thread 230 will have a lead distance double that of a single-start thread of the same pitch, a triple start thread will have a lead distance three times longer than a single-start thread of the same pitch, and so on. The double-start thread adjacent the distal end 260 has constant pitch.

The region 293 includes the single-start constant pitch thread 240 extending to the proximal end. The lead of the screw in the region 291 is L1 which is larger than the lead L2 in the region 293. Hence when the screw is engages with separate portions of the bone a compression is achieved between the bone portions due to the different leads.

FIG. 2B is a sectional view of two bone sections 275 showing the areas that have been cut by the screw including region 291 and region 293. FIG. 2B illustrates the bone screw 201 engaging the two bone sections 275. An advantage of this type of bone screw over a variable pitch bone screw is good bone engagement. In a variable pitch bone screw, no thread exactly follows the thread directly in front of it. In some embodiments herein, the pitch remains constant in region 291 and 293, and hence little or no bone shearing occurs.

In some embodiments, the double-start thread lead distance is double that of a single-start thread. This helps to double the lead without changing the pitch. Due to the double-start or other multi-start at the distal edge, for one rotation, the screw will travel faster than a single-start screw, hence the number of rotations required to insert the screw is low and desirably quick insertion is provided.

The difference in lead between region 291 and region 293 helps to move the two bone fragments at different speeds to generate compression with low bone removal and little or no bone shearing. The double-start that results in a difference in lead between the distal and proximal ends helps to move the two bone fragments at different speeds.

Due to the constant pitch of the threads, a cutting pattern of the distal thread may be followed by the following consecutive threads. Further, constant pitch threads are relatively easy to manufacture. The constant diameter shaft helps to limit the removal of bone material. Also the insertion torque required to place the screws can be low.

The thread heights (distance from crown to root) are constant along the screw in all regions as illustrated; however, differing thread heights or tapered thread heights may be provided. The crest width also is constant along the threaded regions; however variable crest widths may be used.

The transition zone 292 from double-start to single-start is illustrated as having no threads, but it may be threaded with threads matching one or each of the regions 291 and 293. While region 291 is shown as a double-start threaded region, it may be a triple start or greater.

FIG. 2C shows another embodiment of a bone screw using a multi-start thread. The bone screw 202 is similar to the bone screw 201 in FIG. 2A. The bone screw 202 has a constant pitch in region 291 and region 293 and therefore a constant pitch along the length of the thread of the bone screw. Because the pitch in region 293 is the same as the pitch in 291, the thread 240 in region 293 will follow the cuts in the bone made by thread 230. This allows for good purchase between the bone screw 202 and the bone. Further, because of the different lead values in regions 293 and region 291, the bone portions associated with each region will be compressed together.

In other embodiments, a first region of the screw may have a first multi-lead thread with a first lead, and a second region of the screw may have a second multi-lead thread with a second lead that is different than the first lead. This difference in the leads may be due to different numbers of start thread in the regions. The threads in the different regions may have the same pitch to allow for the screw threads in both regions to use the same cuts in the bone.

Some embodiments may provide good levels of compression rate due to the difference in lead, an ability to retain the compression because of low bone shearing, good pullout resistance because no additional bone cut area is created by the proximal threads 240, good thread engagement with the bone due to no bone shearing, quick insertion into bone due to multi-start thread, and good tactile feedback of bone compression due to the higher compression rate.

FIG. 3A through FIG. 3D show embodiments of a bone screw having a step design. The bone screw 301 shown in FIG. 3A is centered on a longitudinal axis 310. The screw 301 has a step design with a first region 391 having constant diameter (D1) from a distal end 360 (in some embodiments for 50% of screw length) and a second region 393 for the remaining length to a proximal end 370 with a constant diameter (D2). The bone screw 301 has a root portion 320 and a thread 330 extending from the root portion 320 in region 391 and a thread 340 extending from the root portion 320 in region 393. The distal end 360 has a self-cutting tip 350.

The first region 391 has two regions 392 and 394. Region 392 has a constant pitch adjacent to the distal end 360. The constant pitch region 392 may include approximately 5 turns. In the constant pitch region 392, the adjacent threads follow the cut profile created by the distal thread in region 392 to avoid bone shearing and provide good purchase and pullout strength. The region 394 is a variable pitch region extending between a transition zone 355 and the constant pitch region 392. The region 393 may have a variable pitch. The proximal end 370 may have a screwdriver socket 371.

Figure 3B:
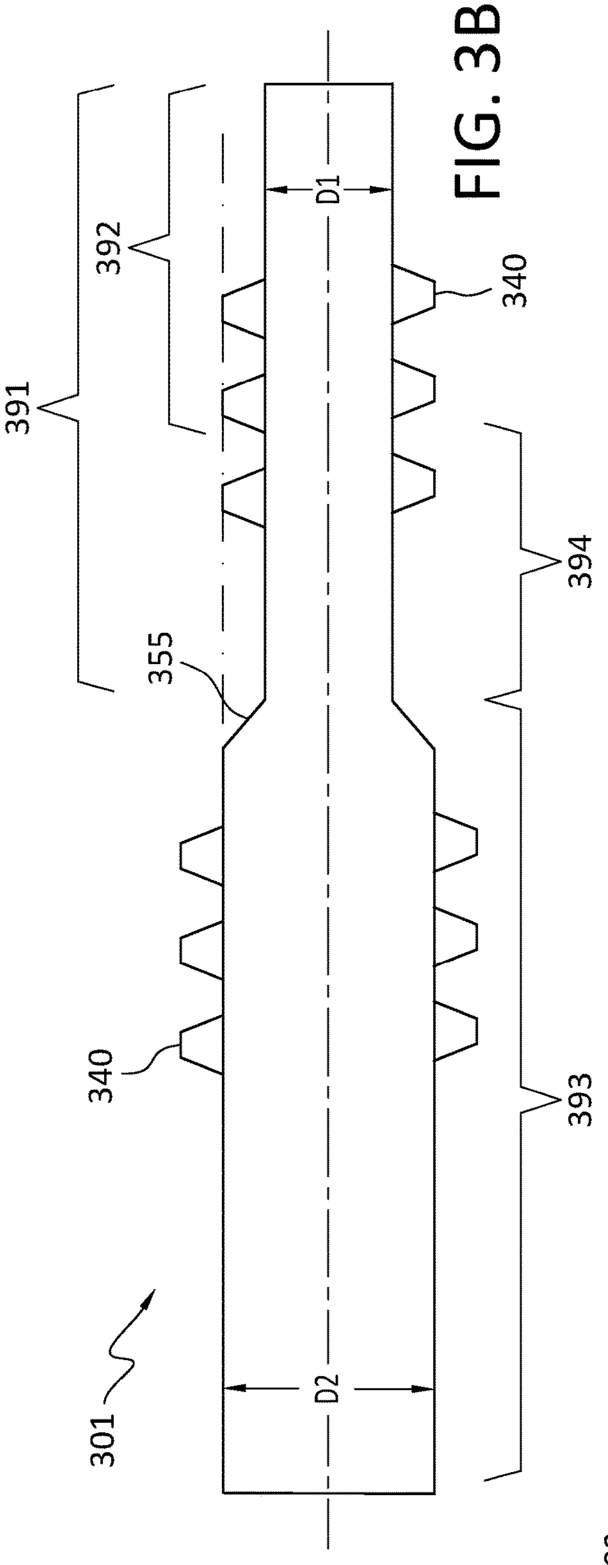
FIG. 3B is a side sectional view of a bone screw.

In some embodiments, the major and minor diameters of the first region 391 are less than the respective major and minor diameters of second region 393. FIG. 3B is a side sectional view of an embodiment of a bone screw with the step design. In FIG. 3B, the major diameter of the region 391 is equal to the minor diameter of the region 393. In other embodiments, the major diameter in region 391 may be greater than or less than the minor diameter of the region 393. The increased diameter in the second region 393 helps to engage the threads with the new bone enabling fresh bone engagement that was not cut by the first region 391. This provides additional purchase with the bone and also helps in avoiding bone shearing and bone blowout.

The relative length of the constant diameter regions 391 and 393 can also vary based on, for example, the screw length or application.

The thread 330 extends continuously, except for a transition zone 355, between distal end 360 and proximal end 370. The threads in the transition zone 355 are removed to avoid sudden increase in the diameter and smooth the transition between region 391 and 392. The transition zone 355 in this embodiment is a tapered step. One or more transition zones implemented as steps may be provided in some embodiments including additional regions with different diameters. The transition zone 355 may be tapered at a selected angle and may be a cylinder or a joining of the threads of regions 391 and 393. The transition zone 355 in alternative embodiments may also include a cutting surface.

As before, the change in pitch from a constant pitch to a variable pitch, causes adjacent bone parts to be drawn together due to the variable pitch.

Figure 3C:
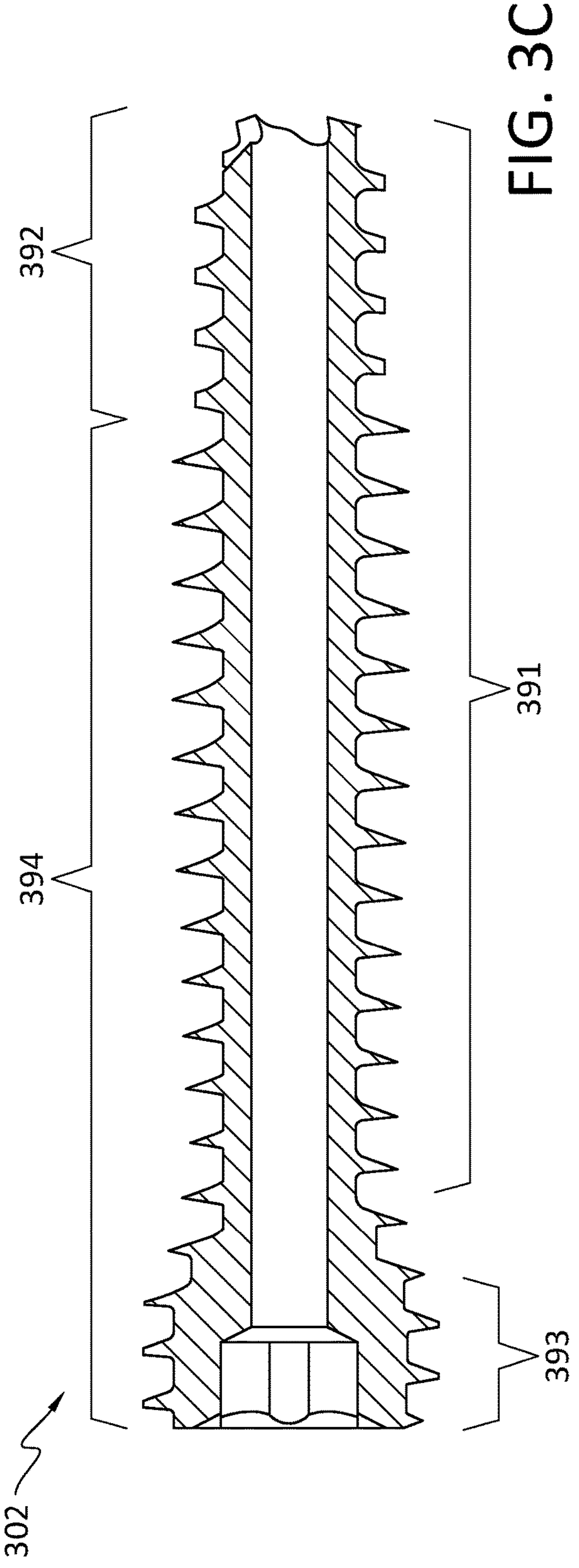
FIG. 3C shows an alternative a bone screw having a step design.

FIG. 3C shows an alternative a bone screw 302 having a step design. The bone screw 302 in FIG. 3C is similar to the bone screw 301 in FIG. 3A. The bone screw 301 has a longer first region 391 and a shorter second region 393. The constant pitch region 392 of bone screw 301 also had a reduction in thread depth versus the thread depth in region 394 having the variable pitch. When inserting the bone screw 301 into bone, the increased diameter in the second region 393 helps to engage the threads with the new bone enabling fresh bone engagement that was not cut by the first region 391. This provides additional purchase with the bone and also helps in avoiding bone shearing and bone blowout.

Figure 3D:
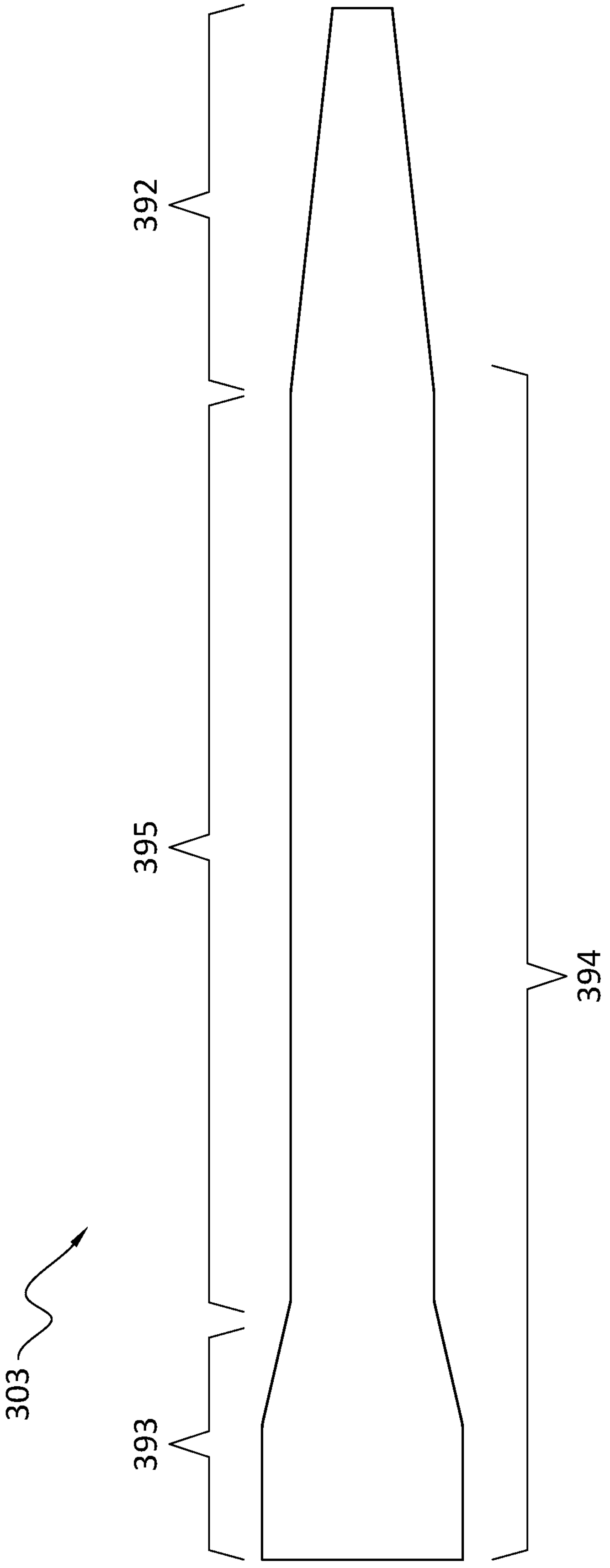
FIG. 3D shows a side profile view of an alternative a bone screw having a step design.

FIG. 3D shows a side profile view of an alternative a bone screw 303 having a step design. The region 392 of bone screw 303 is tapered and has a constant pitch. In this case the region 392 may include five turns. Then the region 395 has a constant diameter with a variable pitch, and region 395 is part of the variable pitch region 394. The transition from the tapered region 392 to the constant diameter region 395 allows for increased engagement with the bone. Finally, a region 393 has an increased diameter like the second region in FIG. 3A. The increased diameter in the region 393 helps to engage the threads with the new bone enabling fresh bone engagement that was not cut by the region 395. This provides additional purchase with the bone and also helps in avoiding bone shearing and bone blowout.

In some implementations, differing thread heights or tapered thread heights can be provided. The crest width also is constant along the threaded regions; however variable crest widths may be used.

Many variations are possible. For example, in any embodiment, the constant pitch threads may include multi-thread pitch threads. Also, one of the threads of the multi-pitch threads may transition into the variable pitch thread. In another example, some or all of the transition regions may be stepped, tapered with no threads, or have threads joining the first region to the second region.

Further, any of the screw embodiments may be cannulated to be used with a guide wire inserted in the bone(s).

The length of the screw, the diameter and lengths of various regions of the screw, and the location of constant and variable pitch regions of the screw may be selected based upon the specific needs in various applications of the screw.

Some implementations may provide improved compression force, good thread engagement with the bone due to the stepped diameter, good distal thread engagement due to constant pitch, good pullout resistance, more bending strength, less thread deformation, and less bone removal.

The descriptions herein refer to regions of some embodiments. The regions are integral parts of the screw and are also discrete regions. However, the regions in many embodiments need not be adjacent each other. Other threaded or non-threaded regions may be provided between or at the ends of any regions. Also, other threaded or non-threaded regions may be provided inside of, or interspersed within, or adjacent any regions.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A medical screw, comprising:

a first region comprising a constant diameter root with a first diameter and a constant pitch thread;

a second region comprising a constant diameter root with the first diameter and a variable thread pitch that joins continuously to the constant pitch thread; and a third region having a tapered root with a tapered diameter and a variable pitch thread that joins continuously to the variable pitch thread of the second region;

wherein the second region comprises more than one turn of the thread with a variable thread pitch;

wherein the screw is a single threaded screw.

2. The medical screw of claim 1, further comprising a cutting tip on the first region.

3. The medical screw of claim 1, further comprising a driving feature on the third region.

4. The medical screw of claim 1, wherein the first region is a distal region and is adjacent the second region at one end thereof.

5. The medical screw of claim 4, wherein the third region is a proximal region and is adjacent the second region at the other end thereof.

6. The medical screw of claim 4, wherein a largest root diameter in the third region is greater than or equal to an outer diameter of the constant pitch thread in the first region.

* * * * *